(12) United States Patent
Chen et al.

(10) Patent No.: US 7,838,857 B2
(45) Date of Patent: Nov. 23, 2010

(54) INSPECTION CONTAINER

(75) Inventors: Zhiqiang Chen, Beijing (CN); Yuanjing Li, Beijing (CN); Li Zhang, Beijing (CN); Xuewu Wang, Beijing (CN); Yumin Yi, Beijing (CN); Longsong Ran, Beijing (CN); Hongxin Wu, Beijing (CN); Lian Wang, Beijing (CN); Quanwei Song, Beijing (CN); Hu Tang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 192 days.

(21) Appl. No.: 12/202,635

(22) Filed: Sep. 2, 2008

(65) Prior Publication Data
US 2009/0065707 A1    Mar. 12, 2009

(30) Foreign Application Priority Data
Sep. 6, 2007    (CN) ...................... 2007 1 0121434

(51) Int. Cl.
*B01L 3/00* (2006.01)
(52) U.S. Cl. .................. 250/526; 250/428; 250/522.1; 422/58; 422/85; 422/99; 422/100; 422/101; 422/102
(58) Field of Classification Search ................ 250/428, 250/522.1, 526
See application file for complete search history.

(56) References Cited

U.S. PATENT DOCUMENTS

| | | | | |
|---|---|---|---|---|
| 4,865,813 A | * | 9/1989 | Leon | 422/101 |
| 5,149,501 A | * | 9/1992 | Babson et al. | 422/58 |
| 5,527,513 A | * | 6/1996 | Burns | 422/102 |
| 5,624,554 A | * | 4/1997 | Faulkner et al. | 210/232 |
| D439,985 S | * | 4/2001 | Sanner | D24/216 |
| 6,277,646 B1 | * | 8/2001 | Guirguis et al. | 436/165 |
| 6,296,764 B1 | * | 10/2001 | Guirguis et al. | 210/323.1 |
| 6,342,183 B1 | * | 1/2002 | Lappe et al. | 422/58 |
| 6,444,174 B1 | * | 9/2002 | Lascombes | 422/102 |
| 6,517,780 B1 | * | 2/2003 | Cortelazzo | 422/102 |
| 6,582,665 B2 | * | 6/2003 | Faulkner | 422/101 |
| 6,964,752 B2 | * | 11/2005 | Lappe et al. | 422/82 |
| 2009/0065707 A1 | * | 3/2009 | Chen et al. | 250/428 |

FOREIGN PATENT DOCUMENTS

| | | |
|---|---|---|
| EP | 0 968 766 A2 | 7/1999 |
| JP | 11-201897 | 1/1998 |
| WO | WO 2006/052247 | 5/2006 |
| WO | WO 2007/072478 | 6/2007 |

* cited by examiner

*Primary Examiner*—David A Vanore
(74) *Attorney, Agent, or Firm*—Westman, Champlin & Kelly, P.A.

(57) ABSTRACT

The present invention discloses an inspection container, comprising: a bottom and a sidewall, said bottom is coupled to one side of said sidewall to form a space, wherein, there are a plurality of protrudes set on the lower surface of said bottom. The inspection container further comprises a division part, which divides said space into a plurality of subspaces. With the solutions according to the present invention, it is possible to meet the requirement for inspecting a plurality of bottles at one time.

16 Claims, 2 Drawing Sheets

INSPECTION CONTAINER

The present application claims priority of Chinese patent application Serial No. 200710121434.7, filed Sep. 6, 2007, the content of which is hereby incorporated by reference in its entirety.

FIELD OF THE INVENTION

The present invention relates to a technical field in which articles are inspected by radiation imaging, more specifically, to a container for use in inspecting liquid articles through rays radiated from ray source.

BACKGROUND OF THE INVENTION

The conventional equipment, which inspects liquid articles through rays radiated by ray source, only inspects single bottle each time, thereby resulting low inspecting efficiency. Moreover, since the inspected articles are directly placed on the rotating stage, for the inspected articles with shapes of slightness and irregularity, it is easy to incur instability during the inspecting, thereby impacting on the inspecting effect, or further prolonging the inspecting time, thus reducing the inspecting efficiency.

SUMMARY OF THE INVENTION

In view of the shortcomings existing in the above prior art, an object of the present invention is to provide an inspection container, which can meet requirements for inspecting multiple bottles at one time.

In an aspect of the present invention, there is provided an inspection container, comprising a bottom and a sidewall, said bottom is coupled to one side of said sidewall to form a space, wherein, single or a plurality of protrudes are set on the lower surface of said bottom.

Preferably, there is a flange set on the other side of the sidewall.

Preferably, the inspection container further comprises a division part, which divides the space formed by the bottom and the sidewall into a plurality of subspaces.

Preferably, the inspection container further comprises an elastic band, a bandage with buckles, and a gripper with springs, set on the inner surface of the sidewall.

Preferably, the inspection container further comprises a strengthening bar set on the outer surface of the sidewall.

Preferably, said single or said plurality of protrudes are distributed along a circle.

Preferably, said division part has a plurality of branches.

Preferably, said division part can be detachable from the bottom and the sidewall or be integrated with the bottom and the sidewall.

Preferably, the sidewall may be made from materials with elasticity.

Preferably, the division part is made from materials with elasticity.

Preferably, a cross section of each branch of said plurality of branches is flat plate-shaped.

Preferably, said sidewall is cone-shaped.

Preferably, said sidewall is column-shaped.

Preferably, said protrudes are cone-shaped.

Preferably, the areas corresponding to said plurality of subspaces, on the upper surface of said bottom, are applied with distinct colors.

Preferably, said sidewall is solid or hollow.

In another aspect of the present invention, there is provided an inspection container, comprising a bottom an a sidewall, said bottom is coupled to one side of said sidewall to form a space, wherein, said inspection container further comprises a division part for dividing said space into a plurality of subspaces.

In another aspect of the present invention, there is provided an inspection container, comprising a bottom an a sidewall, said bottom is coupled to one side of said sidewall to form a space, wherein, said inspection container further comprises an elastic band, a bandage with buckles, and a gripper with springs, set on the inner surface of the sidewall.

In yet another aspect of the present invention, there is provided an inspection container, comprising a bottom an a sidewall, said bottom is coupled to one side of said sidewall to form a space, wherein, said inspection container further comprises a strengthening bar set on the outer surface of the sidewall.

With the multi-bottle inspection container according to the present invention, a plurality of bottles may be inspected each time, thereby improving the efficiency for inspecting articles.

BRIEF DESCRIPTION OF THE DRAWINGS

The above features, advantageous of the present invention will become more obvious from the following detail description given in conjunction with drawings, in which.

DETAILED DESCRIPTION OF THE PREFERRED EMBODIMENTS

Figure 1:
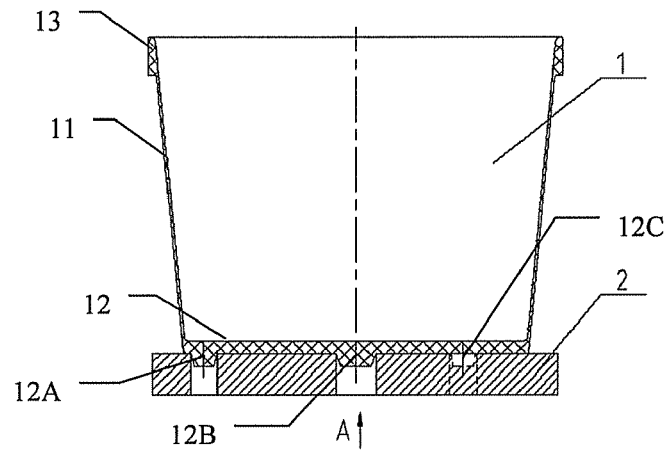
FIG. 1 is a schematic diagram showing a structure for an inspection container according to the first embodiment of the present invention.

Hereafter, preferred embodiments of the present invention will be explained in detail with reference to the drawings. In the drawings, the like reference numbers refer to the same or the like components in the different drawings. For the clarify and simplicity, the detail descriptions for the already known functions and structures herein will be omitted, in order to avoid obscuring the subject matter of the present invention.

FIG. 1 is a schematic diagram showing a structure for an inspection container according to the first embodiment of the present invention. As shown in FIG. 1, an inspection container 1 according to the first embodiment comprises a bottom 12 and a sidewall 11 coupled to the bottom. There are protrudes 12A, 12B and 12C with shapes of the cone or the other, set on the lower surface of the bottom. These three cone-shaped protrudes may be inserted into the corresponding locating holes on a rotating stage 2, such that the inspection container 1 may rotate along with the rotating stage 2 during the rotating process of the rotating stage, thereby preventing relative motions from appearing between them. Additionally, as shown in FIG. 1, there is a flange 13 set on a top circle of the sidewall 11, which is used to facilitate users grabbing and conveying. The sidewall 11 is cone-shaped or column-shaped, and may be made from materials with elasticity, such as polyethylene (PE) or aluminum.

Figure 2:
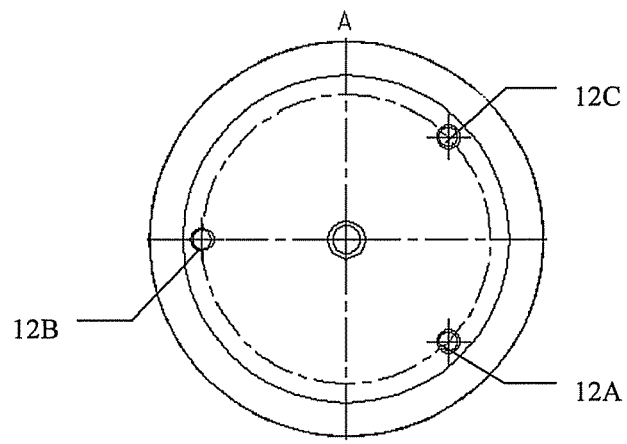
FIG. 2 is an A-sense view for the inspection container shown in FIG. 1.

FIG. 2 is an A-sense view for the inspection container shown in FIG. 1. There are three protrudes 12A, 12B and 12C uniformly distributed on the lower surface of the bottom. However, the distribution for these three protrudes may be nonuniform.

Additionally, there are a plurality of elastic bands, bandages with buckles and grippers with springs (not shown), mounted on the inner side of the sidewall, which are used to temporarily fix the liquid articles to be inspected, such as multi-bottle makeup, on the inner space formed by the bottom 12 and the sidewall 11, so as to facilitate inspection.

Figure 3:
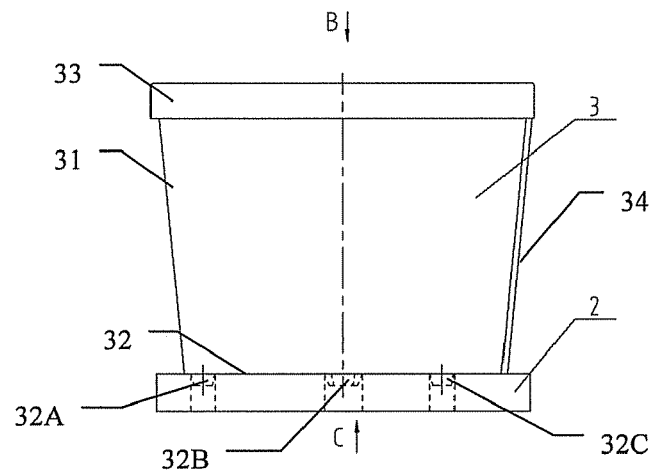
FIG. 3 is a schematic diagram showing a structure for an inspection container according to the second embodiment of the present invention.

FIG. 3 is a schematic diagram showing a structure for an inspection container according to the second embodiment of the present invention. As shown in FIG. 3, an inspection container 3 according to the second embodiment comprises a bottom 32 and a sidewall 31 coupled to the bottom. As such, there are a plurality of cone-shaped protrudes 32A, 32B and 32C, set on the lower surface of the bottom. These three cone-shaped protrudes may be inserted into the corresponding locating holes on the rotating stage 2, such that the inspection container 1 may rotate along with the rotating stage 2 during the rotating process of the rotating stage, thereby preventing relative motions from appearing between them. Additionally, as shown in FIG. 3, there is a flange 33 set on a top circle of the sidewall 31, which is used to facilitate users grabbing and conveying. The sidewall 31 may be made from materials with elasticity, such as polyethylene (PE) or aluminum. Additionally, the sidewall 31 may be hollow. In this way, materials required to manufacture the inspection container may be saved.

Figure 4:
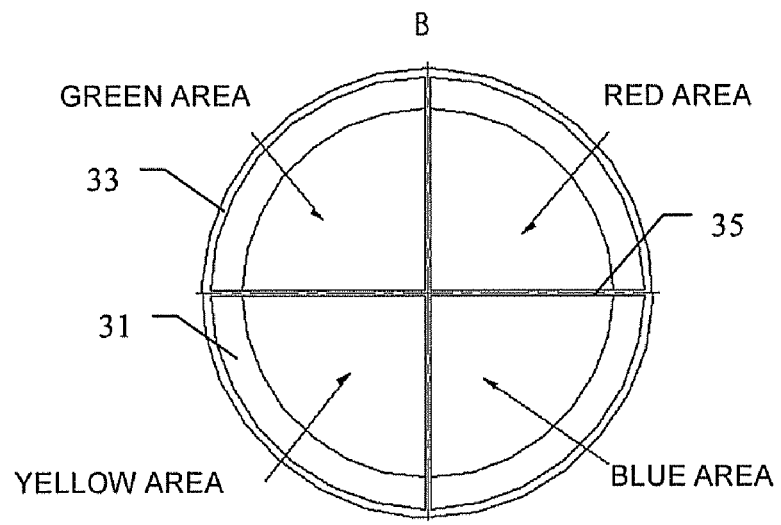
FIG. 4 is a B-sense view for the inspection container shown in FIG. 3.
Figure 5:
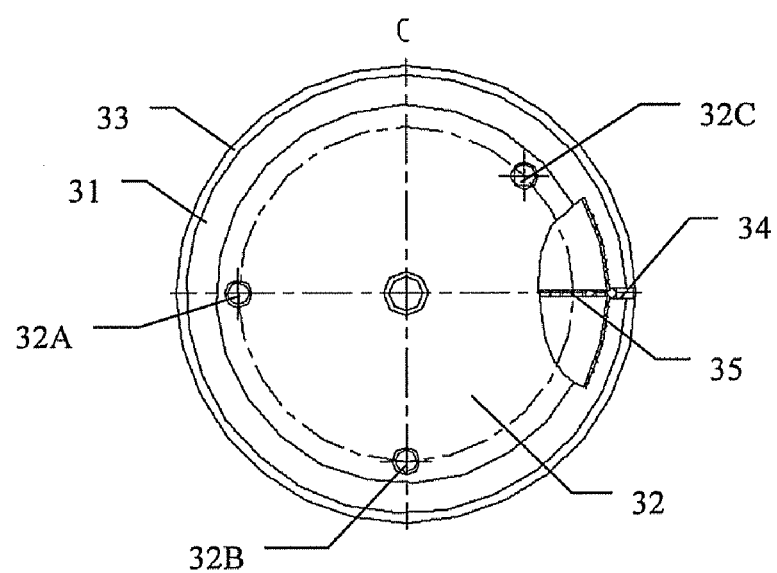
FIG. 5 is a C-sense view for the inspection container shown in FIG. 3.

FIG. 4 is a B-sense view for the inspection container shown in FIG. 3, and FIG. 5 is a C-sense view for the inspection container shown in FIG. 3. As shown, there is a division part 35 set within the space formed by the bottom 32 and the sidewall 31, which is adapted to divide the space into a plurality of subspaces respectively for placing liquid articles, as required. In this way, when a plurality of liquid articles are to be inspected at one time, the plurality of liquid articles are respectively placed in the subspaces divided by the division part 35, where the liquid articles are to be inspected at one time. In this case, there may be a strengthening bar 34 set on the outer surface of the sidewall, which is adapted to facilitate the locating for the articles in the inspection container during the inspecting. For example, when it is inspected that there is one questionable bottle among four articles in the inspection container, it is possible to report to users that which articles is questionable according to the angle that the articles with respect to the strengthening bar set on the sidewall 31.

Additionally, the parts corresponding to the subspaces divided by the division part 35, on the upper surface of the bottom 32, may be applied with distinct colors, so as to further facilitate users distinguishing the respective divided spaces. As shown in FIG. 4, the respective areas on the upper surface of the bottom 32 have been applied with green, yellow, blue and red.

As an alternative, the division part 35 may be detachable from the sidewall 31 and the bottom 32. In this way, in the case of the liquid articles with large size, the liquid articles are directly placed into the inspection container without a division plate, and are temporarily fixed by the elastic band, the bandage with buckles, and the gripper with springs described above, for facilitating inspection. In the case of the articles with relatively small size, the division plate 35 is inserted into the sidewall, so as to divide a large space into small spaces to inspect a plurality of articles by placing them in the corresponding subspaces, thereby improving the inspecting efficiency. Of course, the division part 35 may be not detachable from the sidewall and the bottom. The division part 35 may be made from materials with elasticity, such as polyethylene (PE) or aluminum.

Additionally, the elastic band, the bandage with buckles, and the gripper with springs described above may be applied in the subspaces divided by the division part 35. In this way, even with smaller articles, it is possible to temporarily fix them in the respective spaces.

As described above, since the sidewall 31 may be cone-shaped, a plurality of inspection containers unused may be stacked together, thereby saving the space required to depositing these inspection containers.

As another alternative, the sidewall 31 may also be made into column or square or the other shapes, or the combination of above.

In the above inspection container 3, there may be one or a plurality of division parts 35, which are adapted to divide the inner space of the container into a plurality of subspaces, in order to improve the inspecting efficiency while temporarily fixing the articles. Additionally, it is possible to use the elastic band, the bandage with buckles, and the gripper with springs to fix articles in the inner of the container, and spray coating and marking differently colorful areas, so as to identify locations, while facilitating the placement and fixation for small articles.

Although the respective branches of the division part 35 as shown in the drawings are flat plat-shaped, they may be curved. For example, in the case that the inner space of the container is divided into two subspaces, the division plate 35 may be made curved, the cross section of which may be made S-shaped, such that when inspecting the articles with a column-shaped cross section, the articles may be fixed more firmly.

The foregoing description gives only the preferred embodiments of the present invention. Thus, the ordinary skilled in the prior art will appreciate that, any modification, or local substitution made within the scope of the present invention should belong to the scope defined in the claims of the present invention. Accordingly, the protection scope of the present invention should depend on the protection scope of the claims.

What is claimed is:

1. An inspection container for use in inspecting articles through rays radiated from a source, comprising: a bottom and a sidewall, said bottom is coupled to one side of said sidewall to form a space for placing a plurality of articles, wherein there is one or a plurality of protrudes set on the lower surface of said bottom, and a strengthening bar is set on an outer surface of the sidewall to facilitate locating of an article in the space according to an angle of the article with respect to the strengthening bar set on the sidewall.

2. The inspection container according to claim 1, wherein, there is a flange set on the other side of the sidewall.

3. The inspection container according to claim 1, further comprising an elastic band, a bandage with buckles, and a gripper with springs, set on the inner surface of the sidewall.

4. The inspection container according to claim 1, wherein, said plurality of protrudes are distributed along a circle.

5. The inspection container according to claim 1, wherein, said sidewall is made from elastic materials.

6. The inspection container according to claim 1, wherein, said sidewall is cone-shaped.

7. The inspection container according to claim 1, wherein, said sidewall is column-shaped.

8. The inspection container according to claim 1, wherein, said protrudes are cone-shaped.

9. The inspection container according to claim 1, wherein, said sidewall is solid or hollow.

10. The inspection container according to claim 1, further comprising a division part, which divides the space formed by the bottom and the sidewall into a plurality of subspaces.

11. The inspection container according to claim 10, further comprising a strengthening bar set on the outer surface of the sidewall.

12. The inspection container according to claim 10, wherein, said division part is detachable from the bottom and the sidewall or is integrated with the bottom and the sidewall.

13. The inspection container according to claim 10, wherein, said division part is made from elastic materials.

14. The inspection container according to claim 10, wherein, areas corresponding to said plurality of subspaces, on the upper surface of said bottom, are applied with distinct colors.

15. The inspection container according to claim 10, wherein, said division part has a plurality of branches.

16. The inspection container according to claim 15, wherein, a cross section of each branch of said plurality of branches is flat plate-shaped.

* * * * *